United States Patent [19]

Dykstra et al.

[11] Patent Number: 4,932,936

[45] Date of Patent: Jun. 12, 1990

[54] METHOD AND DEVICE FOR PHARMACOLOGICAL CONTROL OF SPASTICITY

[75] Inventors: Dennis D. Dykstra, Eagan; Abraham A. Sidi, Minneapolis, both of Minn.

[73] Assignee: Regents of the University of Minnesota, Minneapolis, Minn.

[21] Appl. No.: 150,084

[22] Filed: Jan. 29, 1988

[51] Int. Cl.$^5$ .............................................. A61M 31/00
[52] U.S. Cl. ....................................................... 604/51
[58] Field of Search ............................ 128/4, 7, 303.1; 604/51, 27

[56] References Cited

U.S. PATENT DOCUMENTS 4,207,897 6/1980 Lloyd et al. ................... 128/303.1
4,524,770 6/1985 Orandi ............................. 128/303.1

OTHER PUBLICATIONS

Lockart, et al., "Sphincterotomy Failure in Neurogenic Bladder Disease", The Journal of Urology, Jan. 1986; vol. 135, pp. 86–89.
Scott, Alan B., "Botulinum toxin Injection of Eye Muscles to Correct Strabismus", Trans Am. Ophthalmol. Soc., 1981, vol. 79, pp. 734–770.
Webster et al., Medical Instrumentation-Application and Design, 1978; pp. 250, 305–308.
Cromwell et al., Instrumentation For Health Care, 1976; pp. 308–310.
Toxicology Mechanisms and Analytical Methods, vol. 2, 1961; Bensley et al., "the Treatment of Acute Poisoning", p. 833.

Primary Examiner—C. Fred Rosenbaum
Assistant Examiner—Sharon Rose
Attorney, Agent, or Firm—John W. Bunch

[57] ABSTRACT

A method and apparatus for pharmacological control of spastic urethral sphincters, particularly in patients with spinal cord injuries, includes a special monopolar electrode/needle (30) adapted for insertion through a cystoscope (46) in electrical isolation therewith but connection with an electromyograph (12) for precise determination of injection sites so that a toxin, such as botulinum A, can be injected directly into skeletal muscle tissue, rather than connective tissue, to denervate and thus relax the sphincter.

6 Claims, 1 Drawing Sheet

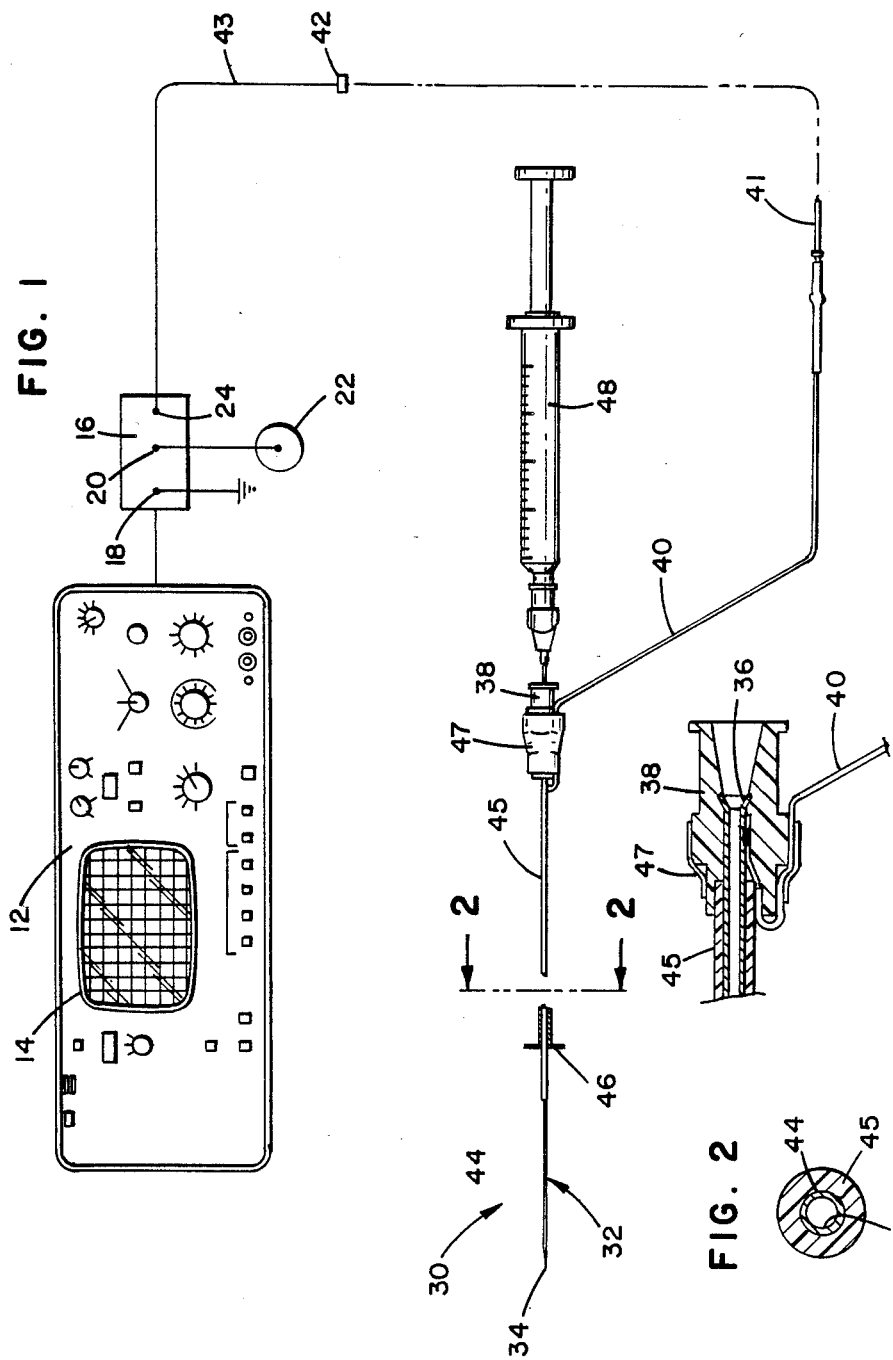

METHOD AND DEVICE FOR PHARMACOLOGICAL CONTROL OF SPASTICITY

TECHNICAL FIELD

The present invention relates generally to a urology technique. More particularly, this invention concerns a method and apparatus for pharmacological treatment of spastic urethral sphincters in patients with spinal cord injuries.

BACKGROUND ART

Patients with spinal cord injuries often develop urinary complications. A spastic urethral sphincter is usually symptomatic of a spinal cord injury due to loss of neural connections between the bladder and central nervous system. Instead of relaxing, the urethral sphincter contracts when the bladder contracts to prevent or at least interfere with the release of urine. This in turn can cause recurrent urinary tract infections with progression to pyelonephritis, stone disease and amyloidosis. Also, when the bladder becomes distended but cannot void the urine therein, this can result in autonomic dysreflexia which is a spike in the patient's blood pressure. Renal failure is a common cause of death in spinal cord injury patients.

Although various bladder management techniques have been available they have not been without their drawbacks. Efforts to relieve bladder spasticity have traditionally been surgical. The surgical procedure, known as an external urethral sphincterotomy, is irreversible but may not always be effective. In one recent study the sphincterotomy failure rate was 25%. Jorge L. Lockart, et al: Sphincterotomy Failure in Neurogenic Bladder Disease, *J. of Urology*, Vol. 135, pp. 86-89, 1986. This is a relatively major surgical procedure with concomitant risk of systemic infection, which many patients would rather not undergo.

Medications are unreliable and the side effects can be troublesome.

Long-term indwelling catheters are convenient, but can lead to chronic urinary tract infections. Periodic self-catherization is difficult for many patients, especially for those with poor hand function. Condom catheters keep patients dry, but do not treat detrusor-sphincter dyssynergia or dysreflexia, if present.

A need has thus arisen for a less invasive, reversible means of relieving bladder spasticity. Intramuscular injection of a toxin, such as botulinum, has been used heretofore to treat strabismus, blepharospasm and torticollis in the eye, face and neck muscles. Alan B. Scott, Botulinum Toxin Injection of Eye Muscles to Correct Strabismus, *Tr. Am. Ophth. Soc.*, Vol. LXXIX, pp. 734-770 (1981). However, the technique described therein is designed for extraocular muscles, which can be readily accessed by the attending physician. Heretofore there has not been available a pharmacological technique for treating the problem of detrusor-sphincter dyssynergia in patients with spinal cord injuries.

SUMMARY OF INVENTION

The present invention comprises an apparatus and method for the pharmocological control of urethral spasticity which overcomes the foregoing and other difficulties associated with the prior art. In accordance with the invention, there is provided an apparatus including a unique needle adapted for cystoscopically injecting toxin into the sphincter at multiple sites under direct visual guidance while simultaneously monitoring sphincter muscle activity during the injection for a maximum effectivity. The needle herein is used in conjunction with a cystoscope and electromyograph. Botulinum A is the preferred toxin. The technique includes visually locating the sphincter through the cystoscope after insertion into the urethra, inserting the needle through the working channel of the cystoscope and visually guiding it into the desired sphincter site, checking the response on the electromyograph to confirm that the tip of the needle is in skeletal muscle tissue rather than connective tissue, injecting an effective amount of toxin directly into the sphincter at that site, withdrawing the needle, and repeating these steps as necessary at another site to denervate and relax the entire sphincter.

A BRIEF DESCRIPTION OF DRAWINGS

A better understanding of the invention can be had by reference to the following Detailed Description in conjunction with the accompanying Drawing, wherein:

FIG. 1 is an illustration of a system incorporating the injection needle/electrode of the invention;

FIG. 2 is an enlarged cross-sectional view taken along lines 2—2 on FIG. 1 in the direction of the arrows; and FIG. 3 is a partial enlarged sectional view of the injection/electrode needle herein.

DETAILED DESCRIPTION

Referring now to the Drawing, wherein like reference numerals designate like or corresponding elements throughout the views, there is shown a system 10 for the pharmacological treatment and control of spastic urethral sphincters incorporating the invention. System 10 is particularly adapted for use with patients having spinal cord injuries. The system 10 includes a conventional two channel electromyograph 12 having an oscilloscope screen and other associated controls, jacks, etc. For example, a model M two channel machine from Teca Corporation of Pleasantville, New York, can be used for the electromyograph 12. A preamplifier 16 is connected to the input of the electromyograph 12. The preamplifier 16, which is also of conventional construction, includes a ground terminal 18, a reference terminal 20 connected to a skin sensor or electrode 22, and an active terminal 24. The electrode 22 is attached to the skin of the patient (and not shown) to provide a reference voltage. The active terminal 24 is connected to a needle/electrode 30 which is specially adapted for location of the urethral sphincter and injection of toxin therein through a cystoscope, as will be explained more fully hereinafter.

The needle/electrode 30 includes a needle 32 with a sharp beveled distal end 34 and a proximal end 36 which is connected to a hub 38. For example, the needle 32 can be 23 gauge stainless steel about 35 cm. in length. The hub 38, in the preferred embodiment is also of stainless steel defining a Luerlock hub, which can be soldered to the needle 32. A wire 40 is soldered or otherwise connected at one end to the hub 38. The other end of wire 40 includes a plug 41 for connection to a connector 42 and extension line 43 leading to the active terminal 24.

In accordance with the preferred construction, the needle 32 is entirely coated with a layer of insulation 44, such as a medical grade tetrafluoroethylene or TEF- LON primer and a base coat over its entire length, except at its distal end 34. A second coat of insulation, such as tetrafluroethylene, is then provided over part of the needle 32 to form an insulative sheath 44 extending from the hub 38 to a point spaced inwardly about 3 cm. from the distal end or tip 34 of the needle. It will thus be appreciated that the needle/electrode 30 functions both as a hypodermic needle and as a monopolar electrode. The purpose of layers 44 and 45 is to insulate and electrically isolate the needle/electrode 30 from cystoscope 46, only part of which is shown in FIG. 1.

If desired, a shrink wrapped sleeve 47 can be provided about hub 38 to help secure wire 40.

Toxin, such as Botulinum A, can be injected through needle/electrode 30 by means of a syringe 48. Botulinum A is preferred because it interferes with acetylcholine release from the nerve terminus, not with acetylcholine storage in the vesicles. Affected muscles gradually lose their ability to contract. The effects of repeated administration are cumulative and a prolonged local effect occurs when injected directly into the muscle.

The apparatus herein is used as follows. A cystoscope 46, only part of which is shown, is first inserted into the urethra of the patient. Any suitable cystoscope having separate visual and working channels can be used. For example, an ACMI cystoscope or another commercially available cystoscope could be used. Such devices typically incorporate fiber optics by which the urethral sphincter can be visually located by the attending physician performing the procedure.

After the cystoscope 46 has been inserted and the sphincter has been visually located through it, the needle/electrode 30 is inserted into the working channel of the cystoscope 50 and guided visually until the distal end or tip 34 of needle 32 is positioned in the sphincter. Since the sphincter is covered with connective and other tissue, the electromyograph 12 will readily indicate whether the needle 32 has been inserted in skeletal muscle tissue, as desired. If not, the needle/electrode 30 can be withdrawn from the sphincter and reinserted at a different site until the electromyograph 12 confirms that it is in muscle tissue.

After the needle 30 has been properly positioned, a suitable dosage of toxin, such as Botulinum A, from syringe 48 is injected through hub 28 and needle 32 directly into the sphincter. Additional injections at two or three more sites spaced about equally around the sphincter are preferably made in the same fashion, following which the needle/electrode 30 and the cystoscope 46 are removed.

The method and apparatus herein have been used experimentally with encouraging results. Our study program included eleven spinal cord-injured men with detrusor-sphinctor dyssynergia who were patients at the Spinal Cord Injury Clinic at the University of Minnesota Hospital, Department of Physical Medicine and Rehabilitation. The men ranged from 21 to 48 years of age (average age 29). The length of time since spinal cord injury ranged from 2 to 15 years (average time 8 years). 10 patients had injuries at the cervical spine level; 8 of those injuries were complete. 1 patient had a complete injury at the low thoracic spine level. All 11 men had been using condom catheters for urine collection.

Treatment was given on an outpatient basis through the clinic's urodynamics laboratory. Before entering the treatment program, a complete medical history was taken and each patient was given a physical examination. Determination of average post-void risidual urine volumes (pvr), cultures of urine samples, systometrography with electromyography (cmg/emg), mechanical and electrical stimulation measurement of bulbosphincteric reflexes (bsr), determination of urethral pressure profiles (upp), excretory urography, voiding cystourethrography and manual muscle tests were also performed for most patients.

Very low doses of Botulinum A toxin were used, with the maximum being less than 4 units per kilogram of body weight.

Three treatment protocols were developed and evaluated. Because the effects of botulinum A toxin are additive with peak effects occurring about 3-4 days after administration, a weekly injection schedule was used in each protocol. Toxin concentration, injection volume, and percutaneous vs. cystoscopic injection were evaluated. Injections were stopped when the pvr no longer decreased.

In the first protocol, an initial dose of 20 units of toxin was injected percutaneously through the perineum into the rhabdosphincter, however, several injections were needed to produce the maximum decrease in pvr because it was difficult to isolate the rhabdosphincter by the perineal approach. Without direct visual guidance it was difficult to discern whether injection into the proper site of the proper muscle occurred.

In the second protocol, an initial dose of 80 units of toxin was injected cystoscopically using an Orandi needle into 3 or 4 sites in the rhabdosphincter, but without monitoring the electromyographic response of the sphincter. However, at least 4 injections were required to produce the maximum decrease in pvr and it was difficult to control precise injection of the toxin into the desired site(s) in the sphincter without electromyographic monitoring.

In the third treatment protocol, an initial dose of 140 units of toxin (5 units per 0.1 cc of normal saline) was injected into the rhabdosphincter through a cystoscope under visual guidance with electromyographic monitoring using the apparatus of the invention herein. A urine sample was taken for culturing before cystoscopy. After cystoscopy, a foley catheter was left in place for 24 hours, and patients were treated prophylactically for four days. All subsequent doses of toxin were 240 units (5 units of toxin per 0.1 cc of normal saline). In this approach, an average of only 3 injections was needed to produce a maximum decrease in pvr. This approach required fewer injections and less toxin.

From the foregoing, it will thus be apparent that the present invention comprises a method and apparatus for pharmocological control of spastic urethral sphincters which incorporates numerous advantages over the prior art. By means of the apparatus herein, the sphincter can first be visually located through a cystoscope and the needle can then be directly inserted therein. Since the needle herein functions also as a monopolar electrode, one can then confirm—by means of the electromyograph—that the needle is positioned in skeletal muscle tissue, rather than connective tissue, for maximum effectivity and control. Other advantages will be evident to those skilled in the art.

Although particular embodiments of the inventioned have been illustrated in the accompanying Drawing and described foregoing Detailed Description, it will be understood that the invention is not limited only to the embodiments disclosed, but is intended to embrace any alternatives, equivalents, modifications and/or rearrangements of elements falling within the scope of the invention as defined by the following claims.

What is claimed is:

1. Apparatus for use with an electromyograph and a cystoscope having separate working and visual channels to effect pharmacological treatment and control of a spastic urethral sphincter, comprising:

a monopolar electrode/needle adapted for insertion through the working channel of the cystoscope, said needle having opposite distal and proximal ends;

the distal end of said monopolar electrode/needle being beveled and sharp;

an insulative sheath on said monopolar electrode/needle, except at the distal end thereof, for electrical isolation from the cystoscope;

means for connecting said monopolar electrode/needle to the electromyograph to confirm when the distal end of said needle has been inserted into skeletal muscle tissue of the urethral sphincter; and means for selectively injecting botulinum A toxin into the proximal end of said monopolar electrode/needle and directly into the sphincter to denervate and relax the sphincter.

2. The apparatus of claim 1, wherein said insulative sheath comprises:

a first coating of tetrafluoroethylene entirely covering said electrode/needle except at the distal end thereof; and a relatively thicker second coating of tetrafluoroethylene covering the first coating from the proximal end to a point spaced a predetermined distance from the proximal end of said electrode/needle.

3. The apparatus of claim 1, wherein the means connecting said electrode/needle to said electromyograph comprises:

a preamplifier having a ground terminal, a reference terminal connected to the patient, and an active terminal; and a lead with one end connected to the electrode/needle and the other end connected to the active terminal of said preamplifier.

4. The apparatus of claim 1, wherein said selective injection means comprises a syringe.

5. A method for pharmacological control of a spastic urethral sphincter, comprising the steps of:

inserting a cystoscope into the urethra, said cystoscope having a working channel and an optical channel;

inserting a monopolar electrode/needle in electrical isolation through the working channel of the cystoscope;

connecting the monopolar electrode/needle to an electromyograph to record muscle activity;

guiding the monopolar electrode/needle through the cystoscope to selective insertion in a site of skeletal muscle tissue as signified by the response on the electromyograph; and injecting an effective amount of botulinum A into the proximal end of the monopolar electrode/needle and into the site to denervate and relax the sphincter.

6. Apparatus for pharmacological treatment and control of a spastic urethral sphincter, comprising:

a cystoscope having separate working and visual channels;

a monopolar electrode/needle for insertion through the working channel of said cystoscope, said needle having opposite distal and proximal ends;

an insulative sheath on said monopolar electrode/needle for maintaining electrical isolation from said cystoscope, except at the distal tip thereof;

an electromyograph for recording muscle activity;

means connecting said monopolar electrode/needle to said electromyograph to confirm when the distal end of said needle has been inserted into skeletal muscle tissue of the urethral sphincter; and means for selectively injecting toxin into the proximal end of said monopolar electrode/needle and into the sphincter to denervate and relax the sphincter.

* * * * *